United States Patent [19]
Wilkins et al.

[11] 3,939,044
[45] Feb. 17, 1976

[54] ANAEROBIC MICROBE TRANSPORT ASSEMBLY AND METHOD OF USING

[75] Inventors: Tracy Dale Wilkins; Franklin Jimenez-Ulate, both of Blacksburg, Va.

[73] Assignee: Virginia Polytechnic Institute Educational Foundation, Inc., Blacksburg, Va.

[22] Filed: Apr. 23, 1975

[21] Appl. No.: 570,641

[52] U.S. Cl. ............... 195/126; 195/127; 195/139
[51] Int. Cl.² ............................................ C12B 1/00
[58] Field of Search ................. 195/127, 139, 126

[56] References Cited
UNITED STATES PATENTS 3,783,106   1/1974   Henshilwood .................. 195/139

*Primary Examiner*—Alvin E. Tanenholtz
*Attorney, Agent, or Firm*—Kane, Dalsimer, Kane, Sullivan and Kurucz

[57] ABSTRACT

Disclosure is made of a novel assembly for transporting anaerobic microbes from clinical patient to laboratory. The assembly provides a convenient and reliable means of maintaining microbial viability in the critical period between collection and deposition in a culturing environment.

26 Claims, 17 Drawing Figures

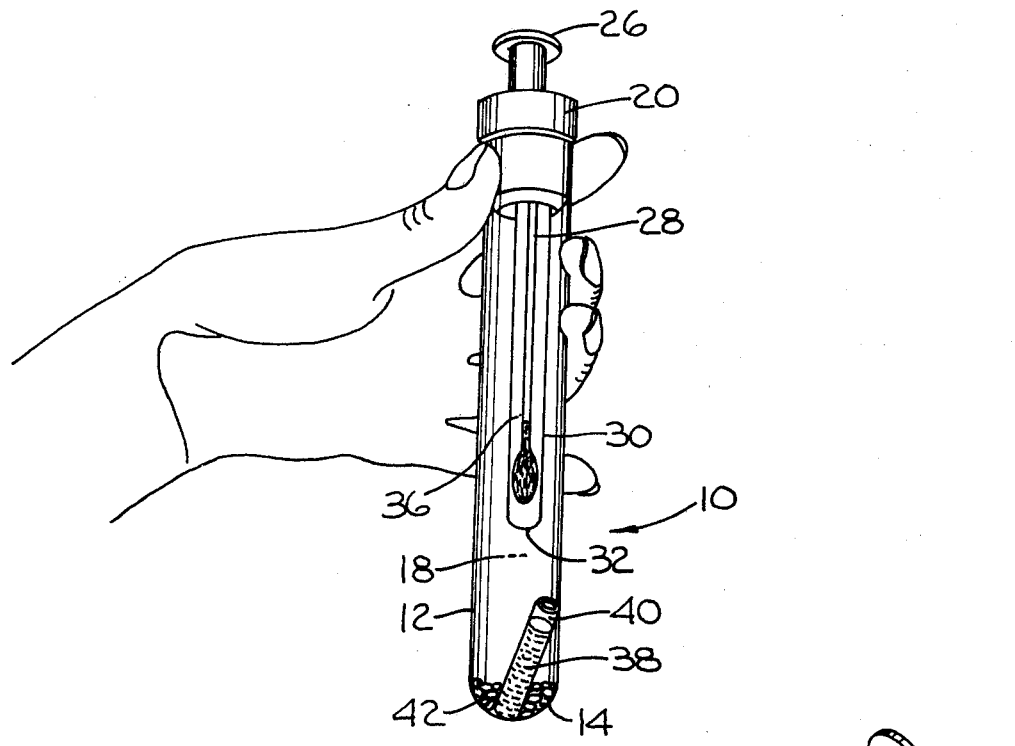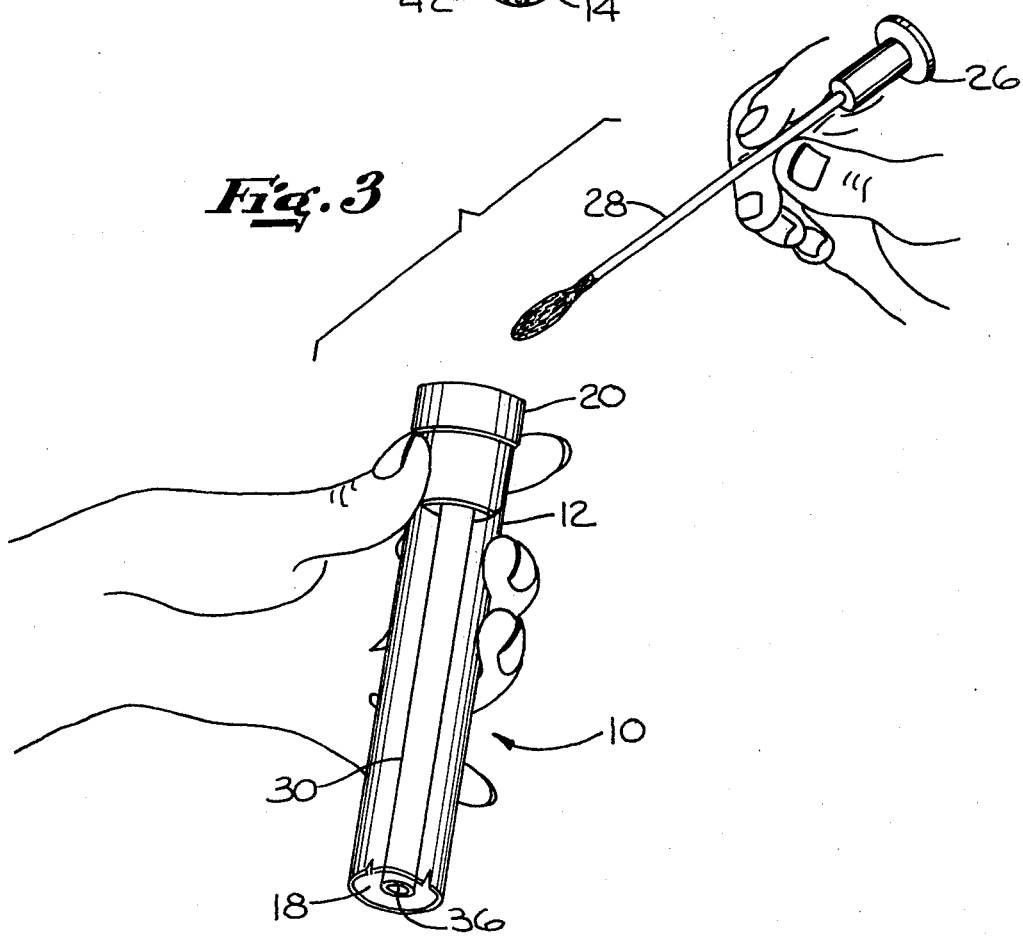

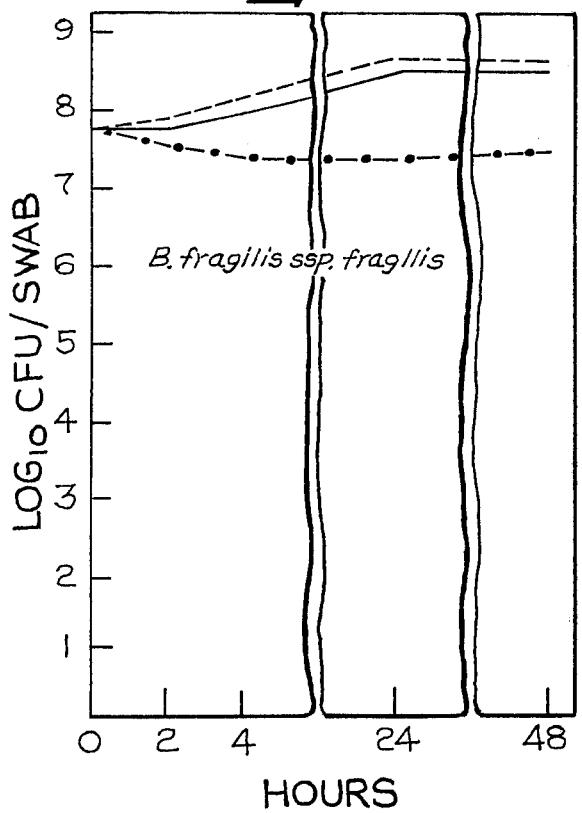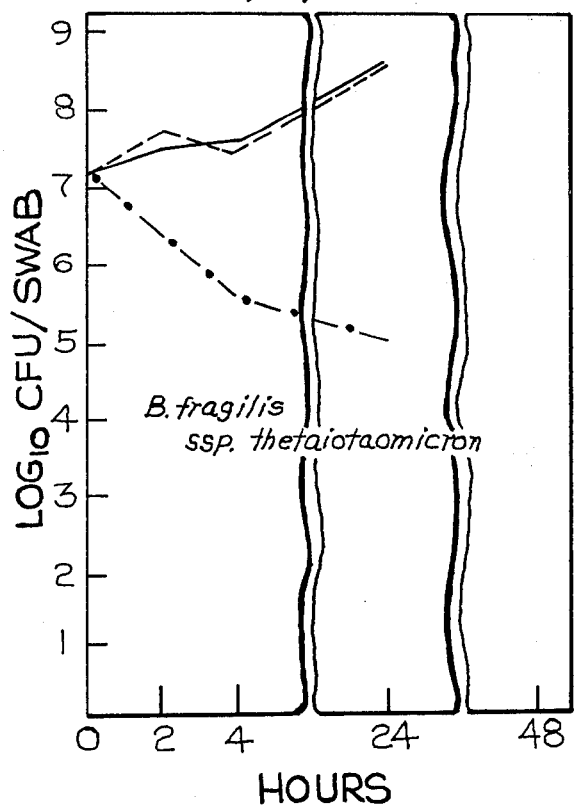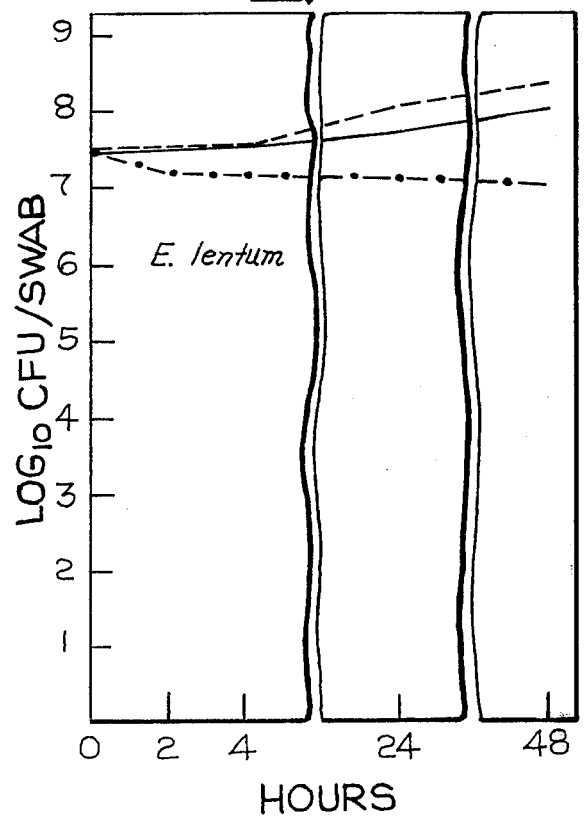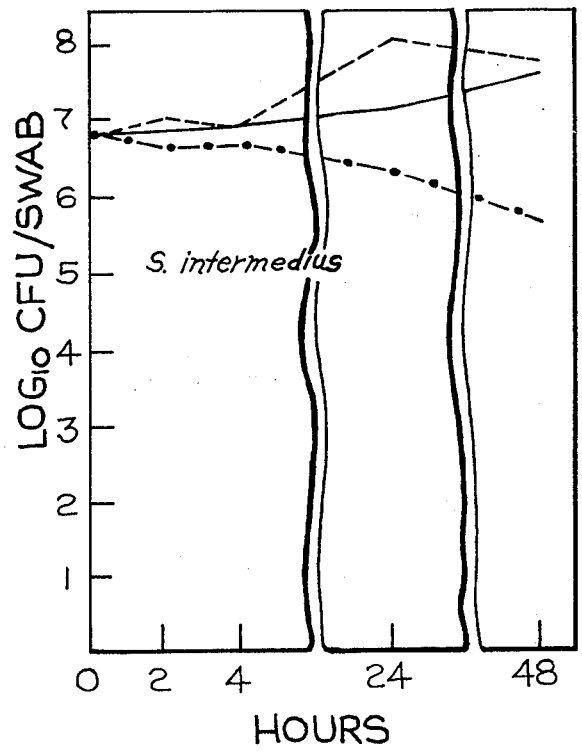

3,939,044

ANAEROBIC MICROBE TRANSPORT ASSEMBLY AND METHOD OF USING

BACKGROUND OF THE INVENTION

1. Field of the Invention

The invention concerns apparatus and methods of culturing microorganisms and more particularly concerns an assembly and the method of its use to protect anaerobes from exposure to gaseous oxygen during the period between isolation from a clinical patient and inoculation into an environment conductive to culturing.

2. Brief Description of the Prior Art

In recent years there has been an increased awareness of the importance of diagnosing anaerobic infections. Apparatus and techniques for culturing and differentiating anaerobes have been developed and refined for diagnosing and differentiating anerobic infections and the causative organisms; see for example the apparatus disclosed in U.S. Pat. No. 3,246,959.

However, the weak link in the overall procedure of collecting a clinical specimen, carrying the specimen to the laboratory and culturing the organisms therein has been in the transportation step. If in transporting the specimen from the clinical patient to the laboratory, the specimen is exposed to gaseous oxygen, the oxygen sensitive anaerobes are eliminated and the subsequent differentiation is inaccurate. Many strains of anaerobes are highly sensitive to oxygen and will not survive even brief exposures to gaseous oxygen.

A review of the prior art methods and apparatus for transporting anaerobes between clinical source and laboratory may be found in the Scope monograph on Anaerobic Infections published by The Upjohn Company, Kalamazoo, Michigan (1972) at pages 54–55 (Library of Congress Card No. 72-79754). In brief, these methods have comprised either rapidly placing a swab collection or specimen in a carbon dioxide filled container, a transport medium, or drawing a liquid specimen into a syringe and then injecting the specimen into an anaerobe bottle. Of these methods, the latter is most likely to maintain strict anaerobiosis provided the specimen is not aspirated with air during collection. The employment of reduced transport medium for anaerobes has not been encouraging; see for example Yrios et al., Abstracts of the Annual Meeting of the ASM, (1974). The Scope monograph reference describes transporting anaerobe suspect organisms on cotton swabs protected from exposure to oxygen by immersion in a pre-reduced, anaerobically sterilized Cary-Blair medium in either a tube or a vial with a mineral oil overlay.

A transporter device is described in U.S. Pat. No. 3,773,035 which is specifically useful in transporting and culturing gonorrhea under a carbon dioxide atmosphere. Other devices representative of the prior art are disclosed in U.S. Pat. Nos. 3,483,089 and 3,750,646.

The method and assembly of the invention incorporates the concept of placing the clinical specimen into an anaerobic environment as rapidly as possible. The methods and apparatus of the prior art all include some time lag in accomplishing this objective. Further, unlike simply placing the clinical specimen into a carbon dioxide filled tube, the amount of air entering the assembly of the invention is limited. The maximum amount of gaseous oxygen to which the specimen is exposed within the assembly of the invention is about 2 percent by volume. This small amount is then rapidly removed as will be hereinafter described.

The apparatus and method of the invention are relatively simple in comparison to the prior art apparatus and methods. The apparatus is constructed readily at low cost and requires a minimum amount of training for operation. In addition, the method of the invention has shown great reliability in operation and assures transportation of viable microbes even for prolonged periods. The assembly of the invention permits one to obtain minimal exposure of a specimen to oxygen.

SUMMARY OF THE INVENTION

The invention comprises an assembly for maintaining anaerobic microorganisms, which comprise; a first tubular container having hermetically sealed ends and which defines a hermetically sealed chamber; means disposed in said chamber for removing gaseous oxygen; a second tubular container having a closed end and an open end and which defines a compartment, said second container being mounted on said first container so that there is no communication between said chamber and said compartment, said compartment being in open communication with the atmosphere outside of said chamber, means of hermetically sealing said open end at will; and means of establishing communication between said chamber and said compartment when said open end is hermetically sealed.

The invention also comprises the method of protecting collected anaerobes by transportation in the assembly of the invention.

The assembly of the invention is also useful for transportation and mantenance of aerobic microorganisms.

BRIEF DESCRIPTION OF THE DRAWINGS

FIG. 2 is an isometric view of the embodiment shown in FIG. 1.

FIG. 3 is an isometric view-in-part as in FIG. 2 showing the swab component withdrawn for isolating a clinical specimen (lower portion of the embodiment not shown).

FIGS. 8a–d are graphs as in FIGS. 6a–d but in relation to anaerobes which are relatively tolerant to oxygen.

DETAILED DESCRIPTION OF THE INVENTION

A complete understanding of the invention may be readily obtained by referring to the preferred embodiment shown in the accompanying drawings of FIGS. 1 – 8, inclusive.

Figure 1:
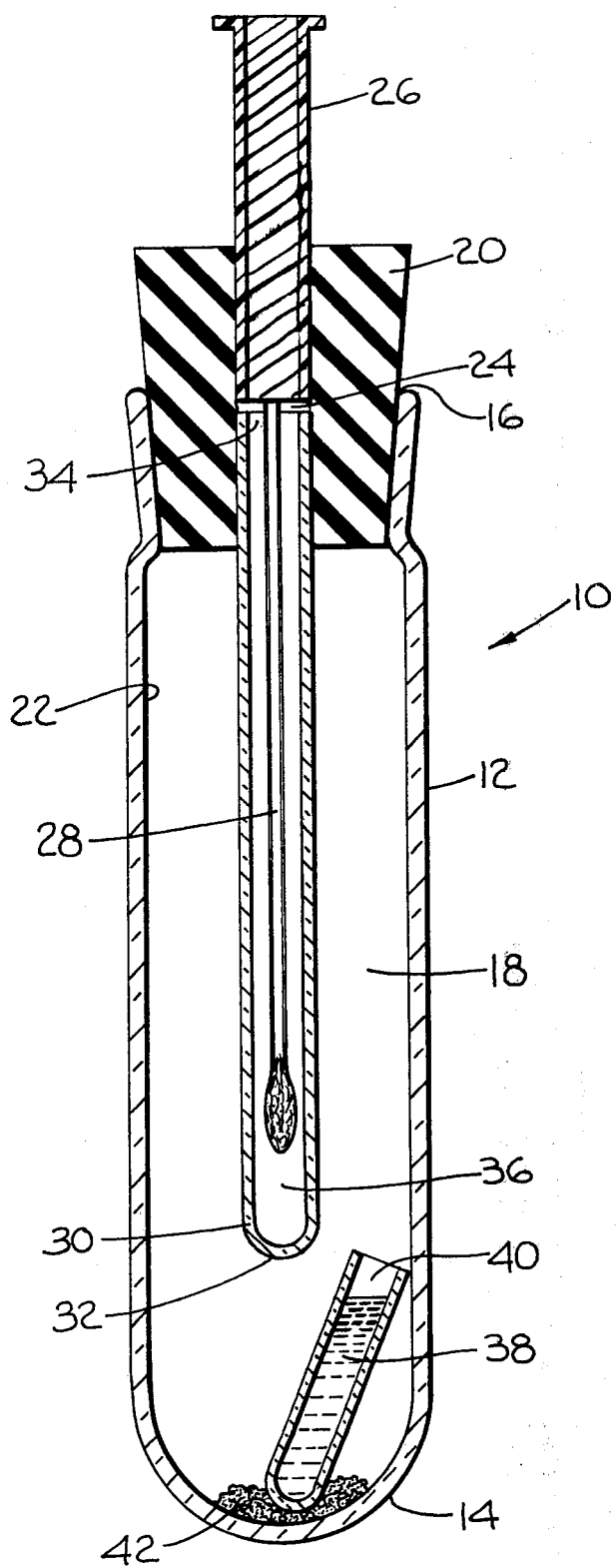
FIG. 1 is a cross-sectional side elevation of a preferred embodiment of the invention.

FIG. 1 is a cross-sectional side-elevation of a preferred assembly 10 which consists of a first tubular container 12 having hermetically sealed ends 14, 16 and defining a hermetically sealed chamber 18. Container 12 may be fabricated from any material conventionally employed to construct laboratory apparatus, such as glass, gas-impermeable polymerics and the like. Preferably the material selected is transparent. End 14 is an integral closed end of container 12 while the end 16 is hermetically sealed with an elastomeric plug 20 in frictional engagement with the inner walls 22 of container 12. A bore 24 traverses plug 20 and would normally provide communication between chamber 18 and the atmosphere outside of container 12 except that bore 24 is closed by closure 26. Closure 26 is a rigid, rod-like plunger extending from a point mid-way through said bore to a point distal to plug 20. The length of closure 26 is at least equal to the length of bore 24 and closure 26 is disposed in a sliding-seal with the inner walls of bore 24 so that closure 26 will maintain the hermetic sealing of chamber 18. Closure 26 is preferably fabricated from a polymeric resin such as polyethylene, polypropylene, polyurethane and the like. Attached at the lower end of closure 26, in the center thereof, is swab 28 for collecting clinical specimens of anaerobes. The length of swab 28 is such that it is less than the length of second tubular container 30 in which it is disposed. Container 30 is mounted by a frictional fit in the lower end of bore 24 so that container 30 also forms a hermetic seal for chamber 18. Container 30 has a hermetically sealed end 32 terminating in chamber 18 and an open end 34 terminating within bore 24. The length of container 30 is less than the longitudinal length of chamber 18. Container 30 defines an interior compartment 36 which forms a housing for swab 28. Generally, chamber 18 and compartment 36 will contain sterile atmospheres, at least initially and before operation of the assembly. The chamber 18 may contain, initially, any gas which is not harmful to anaerobic microorganisms. Preferably, the gaseous atmosphere within chamber 18 will be, initially, a mixture comprising 10 percent hydrogen, 5 percent carbon dioxide and 85 percent nitrogen.

As also shown in FIG. 1 there is an indicator 38 for detecting oxygen. This is a control device and may be, illustratively, a mixture of reazurin (0.01%), cysteine (0.05%), $KH_2PO_4$ (0.6%), $K_2HPO_4$ (0.87%) and agar (0.7%) adjusted to a Ph of 7.0 with potassium hydroxide in an open vessel 40. This indicator mixture is colorless in the absence of oxygen and red in the presence of oxygen.

Loosely disposed in chamber 18 are palladium covered asbestos pellets 42 which will catalyze the reaction of oxygen with hydrogen to yield water.

Referring now to FIGS. 2–5, the operation of the embodiment shown in FIG. 1 will be described. FIG. 2 shows an isometric view of the assembly 10 held by the operator. In this initial provision step, the contents of assembly 10 are sterile and chamber 18 contains a gaseous atmosphere which is not hostile to anaerobic microorganisms. In FIG. 3, closure 26 has been removed with attached swab 28 for the purpose of isolating a test specimen to be cultured, for example a specimen of body fluid or exudate suspected of harboring anaerobes. It is of course not necessary (although advantageous) that the closure 26 and swab 28 be unitary. Closure 26 could be hollow and swab 28 long enough to protrude out of bore 24 (see FIG. 1).

During the period in which closure 26 is removed, the hermetic sealing of chamber 18 is maintained by closure of bore 24 by the upper open end of second container 30. At this point compartment 36 is of course open to the atmosphere and will contain atmospheric gas containing circa 21 percent gaseous oxygen. Compartment 36 preferably is of a minimum size necessary to contain swab 28. There is no communication between compartment 36 and chamber 18 at this stage of the operation of assembly 10.

Figure 4:
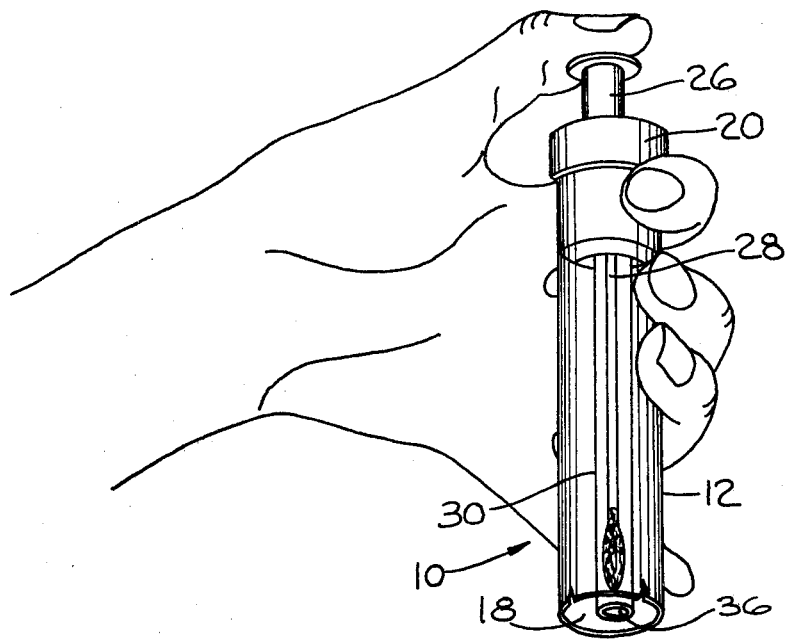
FIG. 4 is an isometric view as in FIG. 3 but following replacement of the swab component.
Figure 5:
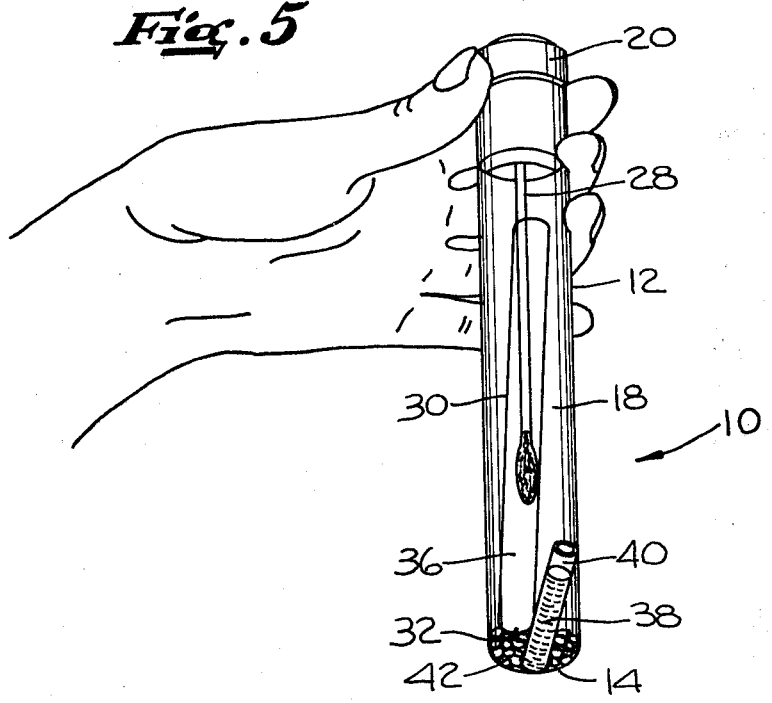
FIG. 5 is an isometric view as in FIG. 4 but after operation to place the collected specimen under anaerobic conditions.
Figure 6A:
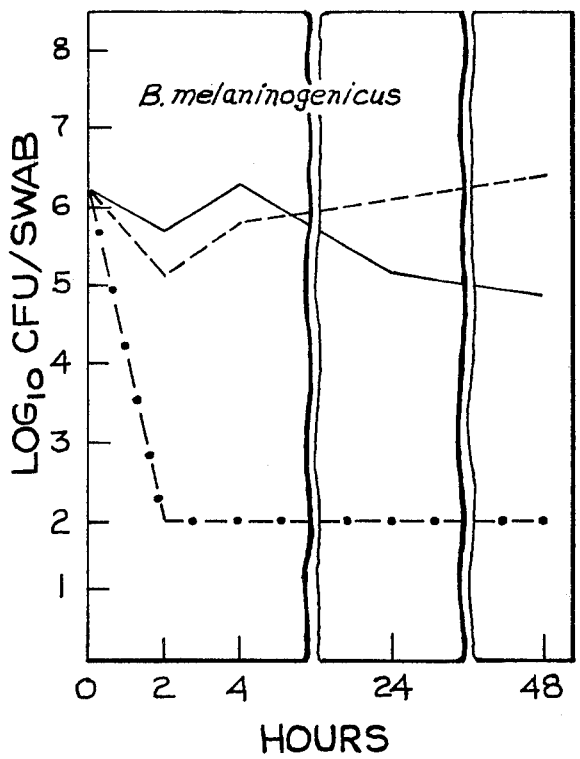
FIGS. 6a–d are graphs showing the survival of oxygen sensitive anaerobes carried on cotton swabs in the assembly of FIGS. 1–5 (solid line), maintained under anaerobic conditions (broken line) and under aerobic conditions (line-dot-line).
Figure 6B:
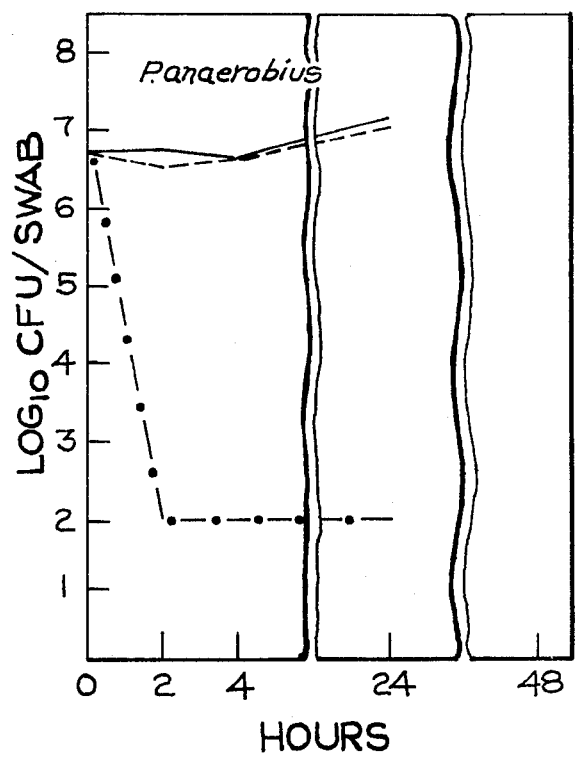
Figure 6C:
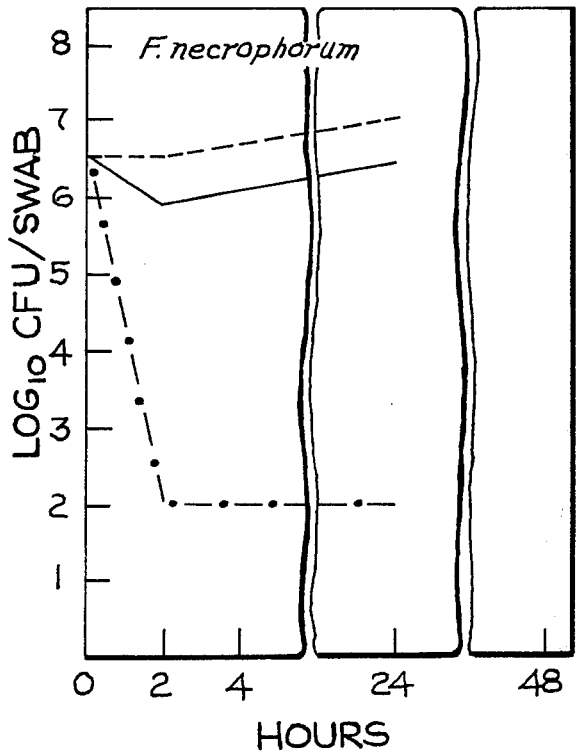
Figure 6D:
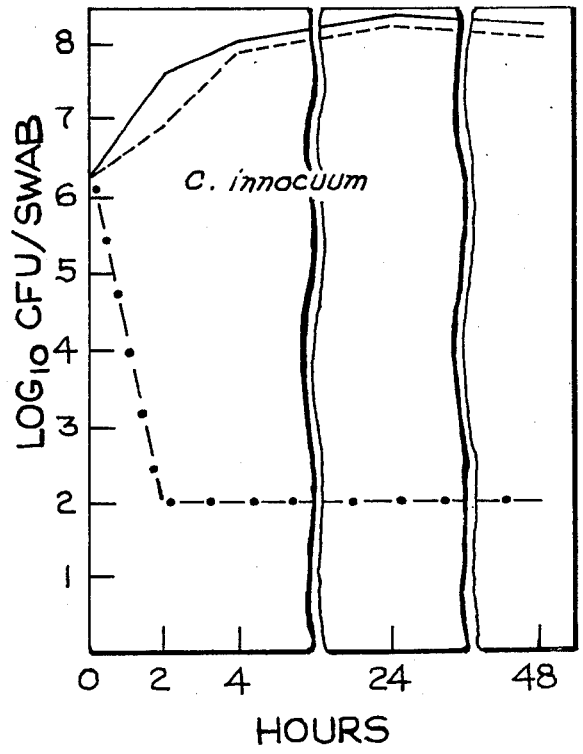
Figure 7A:
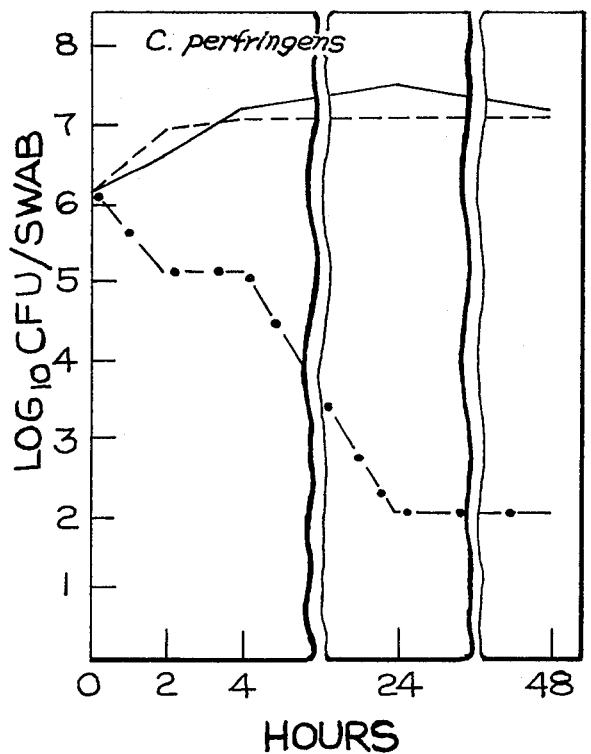
FIGS. 7a–d are graphs as in FIGS. 6a–d but in relation to anaerobes of moderate oxygen sensitivity.
Figure 7B:
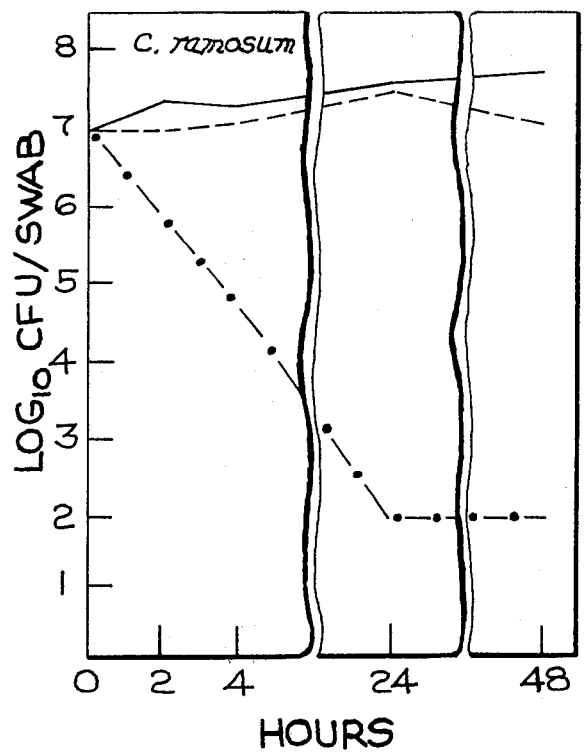
Figure 7C:
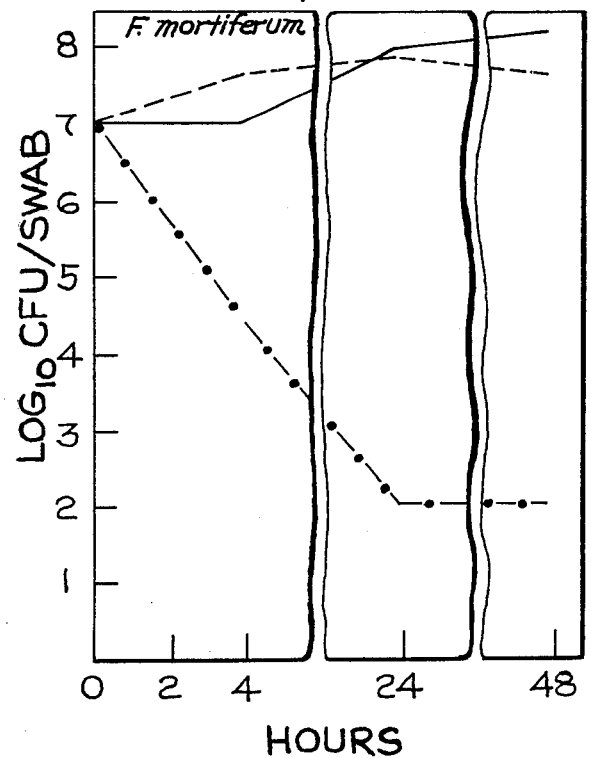
Figure 7D:
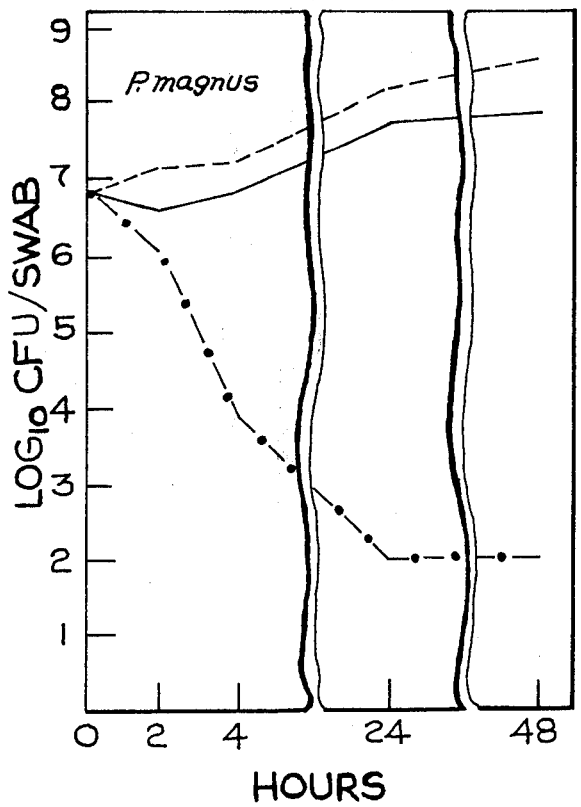

After a test specimen has been isolated on swab 28, the swab 28 is rapidly reinserted in second container 30 as seen in FIG. 4. Immediately upon reinsertion, closure 26 is fully depressed toward container 30 to detach it from engagement with the inner walls of bore 24 to fall into chamber 18. Closure 26 being now fully within bore 24 continues to maintain the hermetic sealing of chamber 18. Chamber 18 is now in open communication with compartment 36 as shown in FIG. 5 and the gaseous atmosphere of chamber 18 mixes with the oxygen containing atmosphere which was bathing, briefly, swab 28. The oxygen now in chamber 18 will cause a positive response to be visually apparent in indicator 38 held in vessel 40. The volumetric capacity of chamber 18 is preferably at least 10 times the volumetric capacity of compartment 36. This ratio provides a dilution of the oxygen from 21 percent of the atmosphere in compartment 36 to about 2 percent or less of the combined atmospheres of chamber 18 and compartment 36. The resulting gas mixture is nonexplosive. Preferably, the resulting gas mixture will contain at least about a two-fold excess of hydrogen over oxygen on a molar basis and most preferably a five-fold excess on an equivalent molar basis.

With admixture of the gases of compartment 36 with the gases of chamber 18, the gas mixture containing both oxygen and hydrogen is brought into the presence of the palladium-on-asbestos catalyst 42. As is well known in the art, such a presence promotes chemical reaction of the hydrogen and oxygen to yield water. The proportion of catalyst 42 employed is a catalytic proportion, readily calculated on the basis of the calculated quantity of oxygen introduced into chamber 18. In this manner, gaseous oxygen is very rapidly removed from chamber 18 and the result is that swab 28 bearing a clinical specimen for future culturing is now bathed by an atmosphere devoid of gaseous oxygen and under substantially atmospheric pressures. If anaerobes are present in the clinical specimen, they are protected from exposure to oxygen and may be safely transported to a laboratory for culturing with conventional techniques and apparatus. With gaseous oxygen removed, reagent 38 is restored to a colorless condition. If for any reason there is a malfunction in the assembly of the invention or its operation so that the atmosphere bathing swab 28 includes oxygen, the operator will be visually alerted by the reagent 38.

Those skilled in the art will appreciate that many modifications may be made to the preferred embodiment described above in relation to FIGS. 1–5, without departing from the spirit of the invention. For example, any other catalyst for the promotion of reaction between hydrogen and oxygen may be employed as can any other means of removing gaseous oxygen from a mixture of gases, e.g. use of an oxygen scavenger compound. Any other means for indicating the presence or absence of oxygen may be substituted for the reagent described above. Also, swab 28 may be eliminated and a clinical specimen deposited directly into compartment 36.

The following preparations and examples describe the manner and process of testing the efficacy of the invention and set forth the best mode contemplated by the inventors of testing the invention but are not to be construed as limiting:

Bacterial Cultures

Anaerobic bacteria are obtained from the culture collection of the virginia Polytechnic Institute Anaerobe Laboratory, Blacksburg, Virginia, and are identified by methods as set forth in the Anaerobe Laboratory Manual, published by the Anaerobe Laboratory of Virginia Polytechnic Institute and State University (V.P.I. Anaerobe Manual).

Aerobic and facultative organisms are from the culture collection of the Biology Department, Virginia Polytechnic Institute, supra.

The Virginia Polytechnic Institute culture collection numbers of the anaerobic bacteria are as follows: *Bacteroides fragilis* ss. *fragilis* 2556-1, *Bacteroides fragilis* ss. *thetaiotaomicron* 5482, *Bacteroides melaninogenicus* ss. *asaccharolyticus* 4198, *Fusobacterium nucleatum* 8748, *Fusobacterium necrophorum*, 6054-A, *Peptococcus magnus* 8352, *Peptostreptococcus anaerobius* 5750, *Streptococcus intermedius* 3372, Eubacterium lentum 1947-1B, *Clostridium ramosum* 8546, *Clostridium innocum* 8593 and *Clostridium perfringens* type A 5201.

Inocula

All cultures are maintained in pre-reduced chopped meat (CM) broth (V.P.I. Anaerobe Laboratory Manual, supra.).

One drop from a Pasteur pipet of an overnight culture in CM broth is added to 10 ml. of pre-reduced Brain Heart Infusion (BHI) broth (V.P.I. Anaerobe Manual, supra.); serial 10-fold dilutions are made in BHI broth, and all tubes are incubated overnight at 37°C. The next day the tube with an optical density nearest to 0.2 but not at maximum turbidity is used as the inoculum. This tube is placed into an anaerobic chamber and 0.2 ml. amounts are placed into the wells of microtiter plates. For aerobic and facultative organisms the above procedure is modified by the use of aerobic BHI medium.

Viable Plate Counts

For anaerobic plate counts, the swabs are taken into the anaerobe chamber and placed into tubes containing 10 ml. of anaerobic dilution fluid (V. P. I. Anaerobe Manual, supra.). The tubes are vigorously agitated on a vortex type mixer and serial ten-fold dilutions made. Duplicate 0.1 ml. amounts of the dilutions are spread on plates of appropriate media. The plates are incubated for 48 hours at 37°C in an incubator contained inside the anaerobic chamber. For aerobic and facultative organisms, the above procedure is modified in that viable plate counts are done aerobically.

Plate Media

Viable plate counts are made on one of the following media according to which gave optimal growth for each organism: Brain Heart Infusion agar (BHIA) with 0.5 percent yeast extract and with and without 5 percent whole sheep blood; Brucella agar with 5 percent whole or laked sheep blood.

EXAMPLE 1

Cotton swabs are placed in each well of the microtiter plates prepared under "Inocula" above, to absorb the inoculum therein. One set of swabs is placed into rubber stoppered tubes and stays inside the glove box as anaerobic controls. Two sets of swabs are taken out of the glove box. One set is immediately inserted into the compartment 36 of the transport devices of the invention as shown in FIG. 1. The other set is placed into aerobic, rubber-stoppered tubes. After 2, 4, 24 and in some cases 48 hours one swab of each type is taken into the glove box and viable plate counts are made from each swab. Following this procedure, a strain of each of twelve specimens of anaerobic microorganisms are isolated and tested for their ability to survive in the assembly of this invention as compared to controls. The results in terms of viable cell counts (detection limit 100 cells per swab) have been graphed in FIGS. 6a–8d, inclusive. The organism is identified on each graph to which it pertains. In the graphs, the solid line indicates the survival of the anaerobes maintained in the assembly of the invention, the broken line indicates the survival of the control anaerobes maintained under anaerobic conditions and the line-dot-line indicates the survival of the microorganisms under aerobic conditions.

FIGS. 6a–d show that with three or four very oxygen-sensitive anaerobes, no significant amount of death occurs prior to the first sample period in the assembly of the invention. With *Fusobacterium necrophorum* there is a loss of viability of approximately half of an order of magnitude by the first sample period, but no further death occurs. *Bacteroides melaninogenicus* is the only culture showing any loss in viability after 24 hours in the device. In all cases, it is evident that viability and survival of the organisms maintained in the assembly of the invention compare favorably with maintenance under strictly anaerobic conditions with absolutely no oxygen contact.

FIGS. 7a–d, showing the results with "moderately-sensitive" anaerobes and FIGS. 8a–d showing the results with anaerobes having a relatively greater tolerance for oxygen also show the survival rate of anaerobes maintained in the assembly of the invention to compare very favorably with survival of the same organisms which were never exposed to oxygen. The assembly of the invention maintained viability of all of the organisms for the length of the test (24 or 48 hours).

The fact that the assembly of the invention adequately protects even the most oxygen sensitive group of clinical anaerobes, which rapidly died on the aerobic control swabs, indicates that anaerobic conditions are attained rapidly in the assembly of the invention. The continued viability of the organisms for 48 hours indicates that desiccation does not occur. Indeed, the conditions within the assembly of the invention are such that most of the organisms continue to grow at the same rate as those on control anaerobic swabs never exposed to air.

Although the invention has been described above with reference to certain embodiments thereof for the purpose of simplicity in description, it should be understood that this invention is in no sense limited thereby and the scope of the invention is to be determined only by that of the appended claims. Many other variations of the invention will be obvious to those skilled in the art, for example the devices of the invention may be provided in any size and any shape. The devices of the invention may also be used to culture anaerobic microorganisms by including a culture medium in container 30 and could also be used to carry out chemical reactions under anaerobic conditions and like variations of use which do not depart from the spirit of the invention.

What is claimed is:

1. An assembly for maintaining anaerobic microorganisms, which comprises;
   a. a first tubular container having hermetically sealed ends and which defines a hermetically sealed chamber;
   b. means disposed in said chamber for removing gaseous oxygen;
   c. a second tubular container having a closed end and an open end and which defines a compartment, said second container being mounted on said first container so that there is no communication between said chamber and said compartment, said compartment being in open communication with the atmosphere outside of said chamber;
   d. means of hermetically sealing said open end at will; and
   e. means of establishing communication between said chamber and said compartment when said open end is hermetically sealed.

2. The assembly of claim 1 which additionally comprises a detector for indicating the presence of oxygen, disposed in said chamber.

3. The assembly of claim 1 wherein said means for removing gaseous oxygen comprises gaseous hydrogen and a catalyst which promotes the formation of water from gaseous hydrogen and gaseous oxygen.

4. The assembly of claim 3 wherein said catalyst is palladium.

5. The assembly of claim 3 wherein said catalyst is palladium on a support carrier.

6. The assembly of claim 1 wherein said second tubular container is mounted on an inner wall defining said chamber.

7. The assembly of claim 1 which additionally comprises a swab withdrawably positioned in said compartment.

8. The assembly of claim 1 wherein one of the hermetically sealed ends of said first container comprises an elastomeric, sealing plug having a bore therethrough, said open end of said second container is frictionally held by the walls of said bore and the means for hermetically sealing said open end comprises a rigid closure member slidably mounted in the bore above said open end, said member forming a sliding-seal with the inner walls of said bore.

9. The assembly of claim 8 wherein said closure member includes a swab attached to one end thereof, said swab extending into the open end of said second container when said closure member seals said open end.

10. The assembly of claim 1 wherein said closure member also additionally comprises said means for establishing communication.

11. The assembly of claim 6 wherein said means for establishing communication comprises a rod communicating between the inside and the outside of said chamber and which when pressed against said second container disengages said second container from its mount on said first container.

12. An assembly for transporting anaerobic microorganisms, which comprises,
   a. a first tubular container having one closed end and one open end and which defines a chamber;
   b. an elastomeric plug hermetically sealing said open end, and having a bore therethrough communicating between said chamber and the outside atmosphere;
   c. means disposed in said chamber for removing gaseous oxygen;
   d. a second tubular container having an open end and a closed end, the open end of said second container being detachably mounted in the lower end of said bore with the closed end of said second container extending into said chamber, said second container defining a compartment; and
   e. a rigid closure member engaged in a sliding-seal with the inner walls of the upper end of said bore, said closure being adapted to move downward to displace said second tubular container.

13. A method of maintaining viability in collected anaerobic microorganisms, which comprises;
   providing an assembly, which comprises: a first tubular container having hermetically sealed ends and which defines a hermetically sealed chamber; means disposed in said chamber for removing gaseous oxygen; a second tubular container having a closed end and an open end and which defines a compartment, said second container being mounted on said first container so that there is no communication between said chamber and said compartment, said compartment being in open communication with the atmosphere outside of said chamber; means of hermetically sealing said open end; and means of establishing communication between said chamber and said compartment when said open end is hermetically sealed;
   depositing a clinical specimen suspected of harboring anaerobic organisms into said compartment;
   hermetically sealing the open end of said compartment; and establishing communication between said chamber and said compartment when said open end is hermetically sealed; and
   activating means for removing gaseous oxygen from said chamber.

14. The method of claim 13 wherein said means for removing gaseous oxygen is simultaneously activated by establishment of communication between said compartment and said chamber.

15. The method of claim 13 wherein said organism is *Bacteroides melaninogenicus*.

16. The method of claim 13 wherein said anaerobe is *Peptostreptococcus anaerobius*.

17. The method of claim 13 wherein said anaerobe is *Fusobacterium necrophorum*.

18. The method of claim 13 wherein said anaerobe is *Clostridium innocum*.

19. The method of claim 13 wherein said organism is *Clostridium perfringens*.

20. The method of claim 13 wherein said anaerobe is *Clostridium ramosum*.

21. The method of claim 13 wherein said organism is *Fusobacterium nucleatum*.

22. The method of claim 13 wherein said anaerobe is *Peptococcus magnus*.

23. The method of claim 13 wherein said anaerobe is *Bacteroides fragilis* ss. *fragilis*.

24. The method of claim 13 wherein said anaerobe is *Bacteroides fragilis* ss. *thetaiotaomicron*.

25. The method of claim 13 wherein said anaerobe is *Eubacterium lentum*.

26. The method of claim 13 wherein said anaerobe is *Streptococcus intermedius*.

* * * * *